US011172884B2

(12) United States Patent
Duan et al.

(10) Patent No.: US 11,172,884 B2
(45) Date of Patent: Nov. 16, 2021

(54) METHOD AND MODULE FOR DETECTING WEARING STATE AND WEARABLE DEVICE

(71) Applicant: Shenzhen Goodix Technology Co., Ltd., Guangdong (CN)

(72) Inventors: Hongliang Duan, Guangdong (CN); Wangwang Yang, Guangdong (CN); Songrong Bai, Guangdong (CN); Chang Liu, Guangdong (CN); Zhiyao Liu, Guangdong (CN)

(73) Assignee: Shenzhen Goodix Technology Co., Ltd., Guangdong (CN)

( * ) Notice: Subject to any disclaimer, the term of this patent is extended or adjusted under 35 U.S.C. 154(b) by 90 days.

(21) Appl. No.: 16/426,224

(22) Filed: May 30, 2019

(65) Prior Publication Data
US 2019/0274628 A1    Sep. 12, 2019

Related U.S. Application Data

(63) Continuation of application No. PCT/CN2018/074009, filed on Jan. 24, 2018.

(51) Int. Cl.
*A61B 5/00* (2006.01)
*A61B 5/024* (2006.01)
(52) U.S. Cl.
CPC ............ *A61B 5/6844* (2013.01); *A61B 5/681* (2013.01); *A61B 5/684* (2013.01); *A61B 5/6843* (2013.01);
(Continued)
(58) Field of Classification Search
CPC ....... A61B 5/6844; A61B 5/681; A61B 5/684; A61B 5/6843; A61B 5/02438;
(Continued)

(56) References Cited

U.S. PATENT DOCUMENTS

| 3,638,640 A * | 2/1972 | Shaw ................. A61B 5/6815 600/323 |
| 2008/0221414 A1* | 9/2008 | Baker ................ A61B 5/14551 600/310 |

(Continued)

FOREIGN PATENT DOCUMENTS

| CN | 203564224 U | 4/2014 |
| CN | 203759644 U | 8/2014 |

(Continued)

OTHER PUBLICATIONS

Extended European Search Report for European Application No. 18880062.7 dated Oct. 11, 2019.
(Continued)

*Primary Examiner* — Nathan J Jenness
(74) *Attorney, Agent, or Firm* — Heslin Rothenberg Farley & Mesiti, P.C.

(57) ABSTRACT

The present disclosure relates to intelligent wearable devices, and provides a method and a module for detecting a wearing state, and a wearable device thereof. The method for detecting a wearing state is applied to the wearable device, and the wearable device includes a light emitter and a light receiver. The detection method includes: controlling the light emitter to emit at least two types of light signals to a user; controlling the light receiver to receive reflected light corresponding to the at least two types of light signals reflected by the user; and determining the wearing state of the wearable device according to change trends of at least two types of the received reflected light. The wearing state of the wearable device is determined more accurately by adopting embodiments of the present disclosure.

11 Claims, 8 Drawing Sheets

(52) U.S. Cl.
CPC ....... *A61B 5/02416* (2013.01); *A61B 5/02438* (2013.01); *A61B 5/7275* (2013.01); *A61B 2560/0276* (2013.01)

(58) Field of Classification Search
CPC ............ A61B 5/02416; A61B 5/14551; A61B 5/1464; A61B 5/6801–6844
See application file for complete search history.

(56) References Cited

U.S. PATENT DOCUMENTS

| | | | | |
|---|---|---|---|---|
| 2009/0306487 | A1* | 12/2009 | Crowe | A61B 5/14551 600/322 |
| 2012/0230699 | A1* | 9/2012 | Burnett | H04R 1/46 398/133 |
| 2014/0176944 | A1 | 6/2014 | Addison et al. | |
| 2014/0275852 | A1* | 9/2014 | Hong | A61B 5/0205 600/301 |
| 2015/0371028 | A1* | 12/2015 | Patel | G06F 21/34 726/16 |
| 2016/0007925 | A1* | 1/2016 | Mirov | A61B 5/6802 356/400 |
| 2016/0287109 | A1* | 10/2016 | Shim | A61B 5/684 |
| 2017/0055907 | A1* | 3/2017 | Altebaeumer | A61B 5/02416 |
| 2017/0071518 | A1* | 3/2017 | Xavier Da Silveira | A61B 5/14552 |
| 2017/0215747 | A1* | 8/2017 | van Dinther | A61B 5/681 |
| 2018/0098708 | A1* | 4/2018 | Lee | G06F 3/011 |
| 2019/0069781 | A1* | 3/2019 | Kim | A61B 5/681 |

FOREIGN PATENT DOCUMENTS

| | | |
|---|---|---|
| CN | 104739386 A | 7/2015 |
| CN | 204708828 U | 10/2015 |
| CN | 105758452 A | 7/2016 |
| CN | 105943014 A | 9/2016 |
| CN | 105979861 A | 9/2016 |
| CN | 106153098 A | 11/2016 |
| CN | 106462685 A | 2/2017 |
| CN | 106647952 A | 5/2017 |
| CN | 107106044 A | 8/2017 |
| CN | 107340708 A | 11/2017 |
| CN | 107436763 A | 12/2017 |
| KR | 10-2013-0043486 A | 4/2013 |
| WO | 2009088799 A1 | 7/2009 |
| WO | 2016167552 A1 | 10/2016 |
| WO | 2017133883 A1 | 8/2017 |
| WO | 2017188540 A1 | 11/2017 |

OTHER PUBLICATIONS

International Search Report in International Application No. PCT/CN2018/074009 dated Sep. 30, 2018.
Office Action in Chinese Application No. 201880000091.5 dated Mar. 25, 2019.
Search Report for Chinese Patent Application No. 201880000091.5 dated Oct. 12, 2019.

* cited by examiner

METHOD AND MODULE FOR DETECTING WEARING STATE AND WEARABLE DEVICE

CROSS-REFERENCE TO RELATED APPLICATIONS

The present application is a continuation of international application No. PCT/CN2018/074009, filed on Jan. 24, 2018, which is hereby incorporated by reference in its entireties.

TECHNICAL FIELD

The present disclosure relates to intelligent wearable devices, and in particular to a method and a module for detecting a wearing state and a wearable device.

BACKGROUND

As wearable products become rich and people pay attention to daily health monitoring, wearable sensors for connecting and detecting biological features are applied more widely. Accuracy of collecting biological signals by wearable products depends heavily on wearing quality of the wearable products. The inventor found following problems in existing technologies: currently-used wearing detection technology has disadvantages of a large wrong determination probability or a long detection time and so on, and existing methods are specifically described below.

In one method of the existing technologies, whether to wear is determined by detecting a signal amount of reflected light from an added LED using a simple optical threshold method. However, this approach may cause a large error. Further, wrong determination may be easily caused because light signal reflection may also occur when a non-skin tissue approaches. In another method, a heart rate signal is monitored based on a characteristic that a device is close to dense blood vessels in a human body after being worn. When the heart rate signal is monitored, it is determined that the device is worn well. However, this method requires continuous operation of a system, leading to a large power consumption.

SUMMARY

An objective of some embodiments of the present disclosure is to provide a method and a module for detecting a wearing state and a wearable device, so that a wearing state of a wearable device can be more accurately determined.

An embodiment of the present disclosure provides a method of detecting a wearing state, which may be applied to a wearable device. The wearable device includes a light emitter and a light receiver. The detection method includes: controlling the light emitter to transmit at least two types of light signals to a user of the wearable device; controlling the light receiver to receive reflected light corresponding to the at least two types of light signals reflected by the user; and determining the wearing state of the wearable device according to change trends of the received at least two types of reflected light.

An embodiment of the present disclosure also provides a module for detecting a wearing state, which may be applied to a wearable device. The detection module includes a light emitter, a light receiver and a processor. The processor is connected to the light emitter and the light receiver respectively, and the processor is configured to control the light emitter to transmit at least two types of light signals to a user, control the light receiver to receive reflected light corresponding to the at least two types of light signals reflected by the user, and determine the wearing state of the wearable device according to change trends of the at least two types of reflected light received by the light receiver.

An embodiment of the present disclosure also provides a wearable device, including the above detection module.

An embodiment of the present disclosure also provides a wearable device, including at least one processor, and a memory connected and communicated with the at least one processor. The memory stores instructions executable by the at least one processor. The instructions are executed by the at least one processor so that the at least one processor is caused to perform the above method for detecting a wearing state.

An embodiment of the present disclosure also provides a computer-readable storage medium storing computer programs, where the computer programs are executed by a processor to implement the above method for detecting a wearing state.

Compared with existing technologies, the wearing state of the wearable device is detected based on an optical characteristic principle of a human tissue in an embodiment of the present disclosure. Specifically, a distance change may be generated between the detection module and the skin during wearing. During the distance change, the wearing state of the wearable device may be determined by detecting change trends of the received reflected light corresponding to at least two types of light signals. Therefore, compared with an existing static detection, the wearing state of the wearable device may be determined more accurately by adopting a dynamic detection, i.e. a dynamically-changing data detection result.

In addition, wavelengths of at least two types of light signals emitted by the two light emitters are different. In this embodiment a wearing detection result may be determined by using the principle of different reflectivities (transmissivities) of light with different wavelengths in the human tissue and on the skin surface, which can be achieved simply and accurately.

In addition, controlling the light emitter to emit at least two types of light signals includes: controlling at least two light emitters to emit at least two types of light signals, where the distances of the at least two light emitters from the light receiver are different. In this embodiment the wearing detection result may be determined based on a principle that attenuations of signals emitted by light sources are different after the signals are reflected and refracted by the skin due to different light paths generated when the distances of the light emitters from the light receiver are different, so that the detection is simple and the result is accurate.

In addition, controlling the light receiver to receive reflected light corresponding to the at least two types of light signals reflected by the user includes: controlling at least two light receivers to receive the reflected light corresponding to the at least two types of light signals reflected by the user respectively. In this embodiment, the reflected light of different light signals is received by different light receivers, thereby reducing mutual interference between the received reflected light.

In addition, controlling the light emitter to emit at least two types of light signals to the user includes: controlling the light emitter to emit at least two types of light signals to the user according to a preset emission period. It is defined in this embodiment that the light signals may be emitted according to the preset emission period rather than emitted in real time, thereby reducing power consumption and avoiding interference between different light signals at the same time.

In addition, each emission period is divided into several emission stages, and the number of emission stages included in each emission period are identical to the type number of the light signals. Controlling the light emitter to emit at least two types of light signals to the user according to the preset emission period includes: controlling the light emitter to emit one type of light signal to the user in each emission stage according to the preset emission period. An emission mechanism of the light signals is further defined in this embodiment: two types of light signals are sent and received in a time division manner, thereby reducing the mutual interference between the light signals.

In addition, when there are two types of light signals, determining the wearing state of the wearable device according to the change trends of the received at least two types of reflected light includes: calculating a difference value of the two types of reflected light, where the difference value is obtained by subtracting a signal amount of one type of reflected light from a signal amount of the other type of reflected light. The wearing state of the wearable device may be determined according to a relationship between the difference value and two preset first signal amount thresholds. It is further defined that the wearing state is determined based on a comparison result of the signal amount difference value and the signal amount thresholds. Thus, the detection process is simple, and the detection result is accurate.

In addition, when there are more than two types of light signals, determining the wearing state of the wearable device according to the change trends of the received at least two types of reflected light includes: determining a relationship between a change trend of a difference value of two types of reflected light selected from the more than two types of light signals and a pre-stored change trend, and determining the wearing state of the wearable device according to a determination result of the change trend; or combining all types of reflected light in pairs, determining a relationship between a change trend of a difference value of each pair of reflected light and a pre-stored change trend respectively, and determining the wearing state of the wearable device according to a determination result of the change trend. A determination method with more than two types of light signals is further defined, so that the determined wearing state is more accurate.

In addition, before the relationship between the change trend of the difference value of two types of reflected light and the pre-stored change trend is determined, following steps may be further included: determining a relationship between the difference value of two types of reflected light and the first signal amount threshold. Determining the wearing state of the wearable device according to the determination result of the change trend includes: determining the wearing state of the wearable device according to a determination result of the relationship between the difference value and the first signal amount threshold and the determination result of the change trend of the difference value. A determination process may be simplified by performing a determination in combination with the difference value and the change trend.

In addition, the wearing state may be divided into N levels, and there are N−1 first signal amount thresholds, where N is a natural number greater than 1. A relationship between the number of preset thresholds and the number of wearing states is defined in the embodiment of the present disclosure, so that the preset thresholds may be set more specifically.

In addition, the wearing state may be divided into three levels, and a higher level corresponds to better wearing quality. The two types of light signals are red light and green light respectively, the difference value is equal to a signal amount of reflected light corresponding to the green light minus a signal amount of reflected light corresponding to the red light, and the two preset first signal amount thresholds are a first threshold and a second threshold, where the first threshold is greater than the second threshold. Determining the wearing state of the wearable device according to the relationship between the difference value and the two preset first signal amount thresholds includes: if the difference value is greater than or equal to the first threshold, further determining the change trend of the difference value including: determining the wearing state as a third-level wearing state if the difference value continuously increases, or returning to determine the relationship between the difference value and the first threshold if the difference value continuously decreases or is unchanged; if the difference value is greater than the second threshold and less than the first threshold, further determining the change trend of the difference value including: determining the wearing state as a second-level wearing state if the difference value is unchanged or decreases, or returning to determine the relationship between the difference value and the second threshold if the difference value continuously increases; and if the difference value is less than or equal to the second threshold, determining the wearing state as a first-level wearing state. It is further defined in this embodiment that at least three wearing states may be determined based on two first signal amount thresholds, and the wearing state may be simply and directly determined by using the threshold comparison method.

In addition, the pre-stored change trend is represented by a feature curve, and the feature curve includes several feature partitions. Determining the relationship between the change trend of the difference value of two types of reflected light and the pre-stored change trend includes: drawing a detection curve according to the difference value of the detected two types of reflected light; and determining which pre-stored feature partition the detection curve belongs to. Determining the wearing state of the wearable device according to the determination result of the change trend includes: determining the wearing state of the wearable device according to the determination result. It is defined in this embodiment that the change trend of the difference value of reflected light is determined based on the feature curve and the divided feature partitions. The wearing state may be obtained more accurately based on the curve, and a richer determination method is provided at the same time.

In addition, the wearing state may be divided into N levels, the N is a natural number greater than 1, and at least one level of the wearing state is "unsuccessful worn". The detection method also includes: determining whether the finally-detected difference value reaches the preset second signal amount threshold when determining which pre-stored feature partition the detection curve belongs to; and if the difference value does not reach the second signal amount threshold, determining that the wearing state of the wearable device is "unsuccessful worn". It is defined in this embodiment that the wearing state is determined as "unsuccessful worn" during wearing detection if it is detected that the difference value is lower than a specific threshold, thereby simplifying a wearing detection process.

In addition, drawing the detection curve according to the difference value of the detected two types of reflected light includes: drawing the detection curve according to the differences value of two types of reflected light detected in the last M detection periods. It is defined in this embodiment that the detection curve is drawn only according to the latest several pieces of detection data. A state closer to a real-time situation may be determined according to the latest data on the precondition of satisfying a determination requirement.

In addition, when the wearable device corresponds to a state flag, determining the wearing state of the wearable device according to the relationship between the difference value and the two preset first signal amount thresholds includes: determining the wearing state of the wearable device according to the relationship between the difference value and the two preset first signal amount thresholds and the state flag. After the wearing state of the wearable device is determined according to the relationship between the difference value and the two preset first signal amount thresholds, a following step may be further included: updating the state flag according to the determined wearing state. It is further defined that the wearable device is provided with the state flag indicating a current state of the wearable device. A determination may be performed in combination with the current state during a determination process, so that the determination result is more accurate.

In addition, the wearable device further includes an acceleration sensor. Before the light receivers are controlled to receive the reflected light corresponding to at least two types of light signals reflected by a user, a following step may be further included: controlling the acceleration sensor to detect an acceleration change. Determining the wearing state of the wearable device according to the change trends of the received at least two types of reflected light includes: determining the wearing state of the wearable device according to the change trends of the received at least two types of reflected light and the acceleration change detected by the acceleration sensor. In this embodiment, the acceleration sensor is added to perform the determination in combination with a light signal detection, so that the detection result is more accurate.

In addition, before determining the wearing state of the wearable device according to the change trends of the received at least two types of reflected light, a following step may be further included: detecting a heart rate signal. Determining the wearing state of the wearable device according to the change trends of the received at least two types of reflected light includes: determining the wearing state of the wearable device according to the change trends of the received at least two types of reflected light and a detection result of the heart rate signal. In this embodiment, a heart rate signal detection is further added to further determine the light signal detection result, so that the obtained detection result of the wearing state is more accurate.

In addition, the detection module further includes a light isolation component connected with the light emitter. In this embodiment, the light isolation component is added to define a shape of light emitted by the light emitter and prevent a large amount of light leakage caused when an optical structure is tightly attached to skin, thereby ensuring a wearing detection effect.

BRIEF DESCRIPTION OF DRAWINGS

One or more embodiments will be illustrated with pictures in corresponding accompanying drawings, and these illustrative descriptions do not constitute limitations to the embodiments. Elements with the same reference numerals in the accompanying drawings represent similar elements. The pictures in the accompanying drawings are not limited in proportions, unless stated otherwise.

DETAILED DESCRIPTION

To understand objectives, technical solutions and advantages of the present disclosure more clearly, some embodiments of the present disclosure will be further described in detail below in combination with drawings and embodiments. It should be understood that the specific embodiments described herein are only configured to explain the present disclosure rather than limit the present disclosure.

Figure 1:
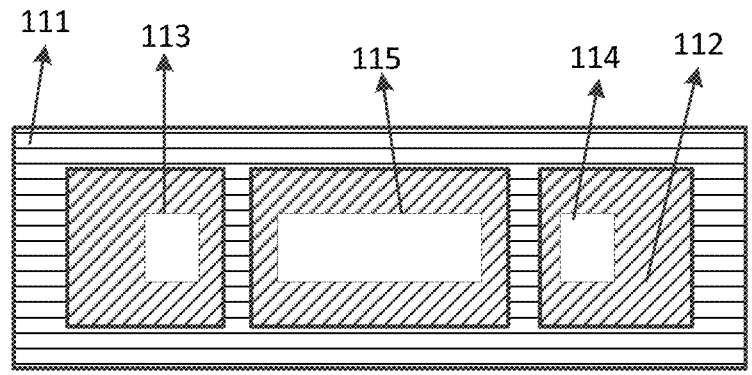
FIG. 1 is a schematic diagram illustrating a detection module according to a first embodiment of the present disclosure.

A first embodiment of the present disclosure relates to a method for detecting wearing state, which may be applied to a wearable device. As shown in FIG. 1, the wearable device includes two light emitters (LED 113 and LED 114) and one light receiver (hereinafter referred to as "PD") 115. It should be noted that the wearable device in this embodiment further includes a light isolation component 111 and a carrying plate 112. The light isolation component 111 is mainly used to isolate a LED light, and the carrying plate 112 is mainly used to carry and fix the LED 113, the LED 114, the PD 115 and the light isolation component 111.

Figure 2:
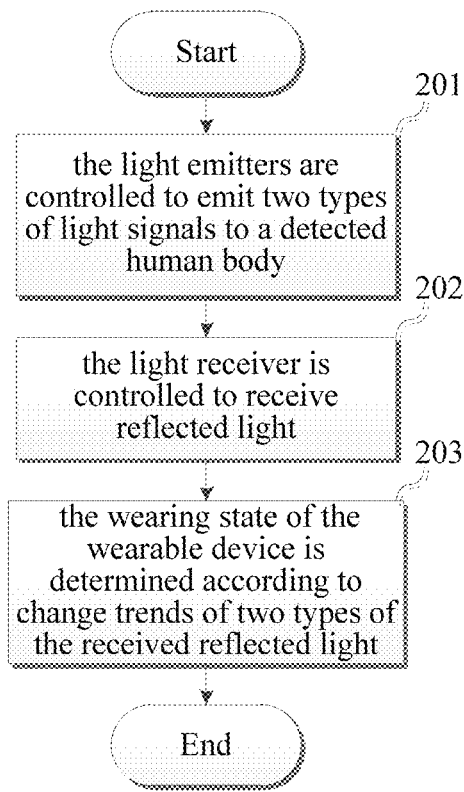
FIG. 2 is a flowchart illustrating a method for detecting a wearing state according to the first embodiment of the present disclosure.

As shown in FIG. 2, the flowchart in this embodiment includes the following steps.

At step 201, the light emitters are controlled to emit two types of light signals to a user of the wearable device.

Specifically, the user may be a person using the wearable device, that is, a person who wears the wearable device. A wearing state of the wearable device relative to this person is required to be detected in this embodiment.

More specifically, in this embodiment, wavelengths of light signals emitted by two light emitters are different, that is, the LED 113 emits a green-light signal (e.g., 525 nm), and the LED 114 emits a red-light signal (e.g., 631 nm). More specifically, the light isolation component 111 is mainly used to control a shape of a light beam emitted by the light emitters. A light isolator may be adopted in this embodiment. The light isolator is a passive optical device allowing only a unidirectional light to pass through, and operates based on a working principle that light echoed and reflected by an optical fiber can be well isolated by the light isolator based on non-reciprocity of Faraday rotation. The light isolator is a passive optical device allowing light to pass through in one direction and preventing light from passing through in an opposite direction, and thus a function of the light isolator is to transmit light only in a single direction by limiting the light direction. Therefore, the light echoed and reflected by the optical fiber can be well isolated by the light isolator, thereby improving light wave transmission efficiency. In this embodiment, a large amount of light leakage caused when an optical structure is tightly attached to skin may be prevented, thereby ensuring a wearing detection effect.

At step 202, the light receiver is controlled to receive reflected light.

Specifically, the light receiver is controlled to receive the reflected light corresponding to two types of light signals reflected by the user. More specifically, the PD receives a red-light signal and a green-light signal. More specifically, in a practical application, the light receiver may be controlled to receive the light signals emitted from two light emitters respectively according to a preset detection period, where the detection period may be 100 microseconds.

At step 203, the wearing state of the wearable device is determined according to change trends of the two types of received reflected light.

Specifically, the wearing state of the wearable device may be determined according to a difference value of signal amounts of the received reflected light corresponding to two types of light signals and two preset first signal amount thresholds. The wearing state may be divided into N levels, and there are N−1 first signal amount thresholds, where the above N is a natural number greater than 1. More specifically, the wearing state may be divided into three levels, and a higher level corresponds to better wearing quality. The two types of light signals are a red light and a green light respectively, the difference value is a signal amount of reflected light corresponding to the green light minus a signal amount of reflected light corresponding to the red light, and the two preset first signal amount thresholds are a first threshold and a second threshold, where the first threshold is greater than the second threshold. Determining the wearing state of the wearable device according to the difference value and the two preset first signal amount thresholds includes: if the difference value is greater than or equal to the first threshold, further determining a change trend of the difference value including: determining the wearing state as a third-level wearing state if the difference value continuously increases, or returning to determine a relationship between the difference value and the first threshold if the difference value continuously decreases or is unchanged; if the difference value is greater than the second threshold and less than the first threshold, further determining the change trend of the difference value including: determining the wearing state as a second-level wearing state if the difference value is unchanged or decreases, or returning to determine the relationship between the difference value and the second threshold if the difference value continuously increases; and if the difference value is less than or equal to the second threshold, determining the wearing state as a first-level wearing state.

For embodiment, three wearing states may be "falling off" (the first-level wearing state), "well worn" (the third-level wearing state) and "being worn" (the second-level wearing state) respectively. Two types of light signals are a red light and a green light respectively, and the two first signal amount thresholds may be set by simulation or according to experience of a technician. The changes of the signal amounts of the reflected light corresponding to two types of light signals are compared with the two preset first signal amount thresholds by using a method below.

A difference value S is obtained by subtracting the signal amount of the red light from the signal amount of the green light. The difference value S may be compared with a preset first threshold A1 and a preset second threshold A2, where A1 is greater than A2. When S≥A1, a change trend of S is further determined: if S continuously increases, it is determined that the wearing state is "well worn"; or if S continuously decreases or is unchanged, a return is made to determine a relationship between S and A1. When A1>S>A2, the change trend of S is further determined: if S is unchanged or decreases, it is determined that the wearing state is "being worn"; or if S continuously increases, a return is made to determine the relationship between S and A2. When S≤A2, it is determined that the wearing state is "falling off".

It is worth mentioning that jitter is allowed to be present in the above trends of continuously increasing, continuously decreasing and so on within a particular range and can be actually removed based on an algorithm, which will not be described herein.

Figure 3:
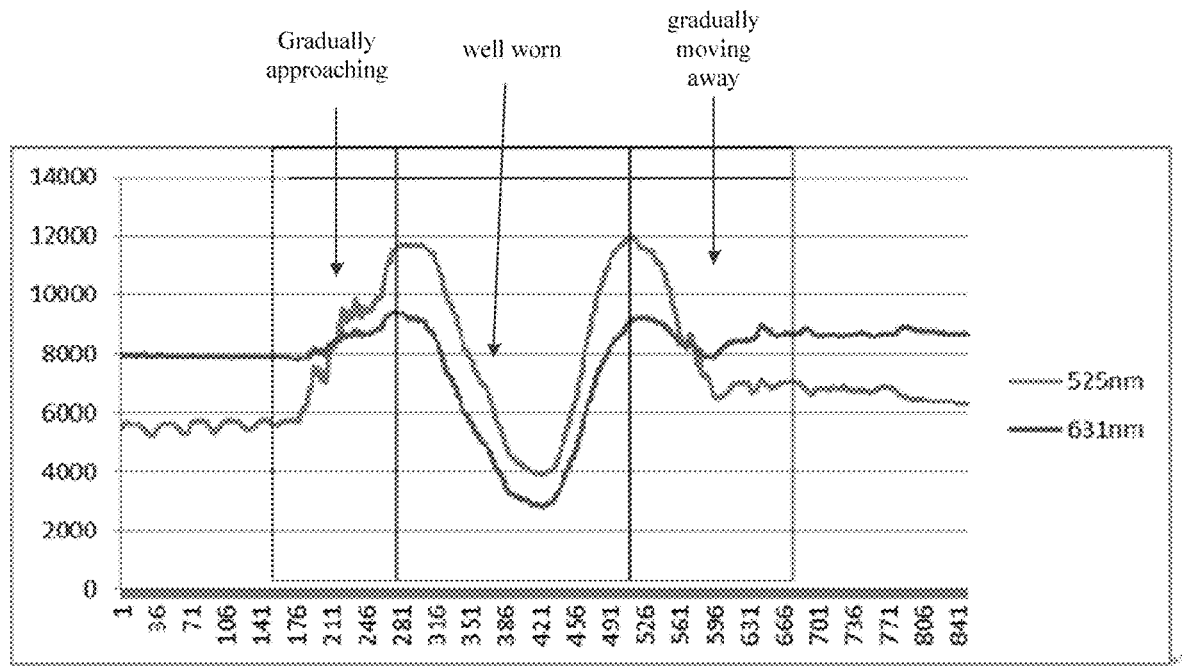
FIG. 3 is a schematic diagram illustrating changes of detected reflected light types of light signals according to the first embodiment of the present disclosure.

The inventor of the present disclosure found that whether the wearable device is approaching or moving away from a human body may be determined according to the received values of the PD since absorptivities and reflectivities of human tissue to light signals with two wavelengths are different due to different optical characteristic principles of the red light and the green light. Therefore, the inventor of the present disclosure obtains a data feature diagram as shown in FIG. 3 by detecting the red-light signal and the green-light signal and classifying a result based on "gradually moving away" and "gradually approaching". It is worth mentioning that the change trend of the reflected light may be represented by using the following parameters: light intensity, light brightness and light illuminance. In a practical application, the above parameters may be adopted separately or in combination, which are not limited herein.

Meanwhile, it may be seen from FIG. 3 that a curve 301 is a curve of the signal amount of the reflected light corresponding to the green light, and a curve 302 is a curve of the signal amount of the reflected light corresponding to the red light. By comparing two curves, curvatures and peaks of both curves are obviously different in presence position when a distance between the wearable device and the human body dynamically changes (during a detection). Therefore, whether the wearable device is approaching or moving away from the human body may be determined by determining whether curvature changes of two types of light signals during a detection are consistent.

It may also be seen from FIG. 3 that data of both a LED emitting a red light and a LED emitting a green light present a trend of first increasing and then decreasing, but the data of the LED emitting the green light changes more obviously when the wearable device gradually moves away from the skin. Since a difference value of the data of the LED emitting the red light and the data of the LED emitting the green light may be different depending on a distance between the wearable device and the skin, a wearing detection may be performed according to the difference value of the LED emitting the red light and the LED emitting the green light. Specifically, when the LED emitting the red light and the LED emitting the green light are adopted, a wavelength difference value of the light signals emitted by the LEDs is about 106 nm, but the wavelength difference value of two LEDs adopted in a practical application may be another value, for embodiment, the difference value may be a value greater than or equal to 50 nm. It is to be noted that the larger the wavelength difference value is, the more accurate the wearing detection result is.

As can be seen, when there are two types of light signals, and step 203 may include: calculating the difference value of two types of the reflected light, where the difference value is a difference value obtained by subtracting a signal amount of one type of the reflected light from a signal amount of the other type of the reflected light. The wearing state of the wearable device may be determined according to the relationship between the difference value and the two preset first signal amount thresholds.

The wearable device in this embodiment may be different in the optical structure, the brightness of the LED emitting the red light and the LED emitting the green light, and the like. When the distance between the wearable device and the skin is given, an absolute value of the LED emitting the red light and the LED emitting the green light may be different, thereby leading to a different difference value of the LED emitting the red light and the LED emitting the green light. When the structures and the brightness of the LED emitting the red light and the LED emitting the green light are fixed, the distance between the wearable device and the skin may be determined according to the received reflected light corresponding to light signals emitted by two LEDs, thereby determining an attaching degree of the wearable device and the skin. When the received reflected light changes, the wearing and falling-off detection of the wearable device may be determined according to the change trends of the two types of reflected light.

In the above descriptions of steps 201-203, the wearing state is detected according to the signal amount thresholds when one LED emitting the red light and one LED emitting the green light are adopted. In a practical application, a light signal emitter emitting a light signal of another wavelength may also be adopted, and the wearing state may be detected by adjusting the signal amount threshold according to an actual situation. In addition, a determination may also be performed by determining whether peaks of signal amounts are consistent in presence position and so on, so that a determination result is more accurate.

Figure 4:
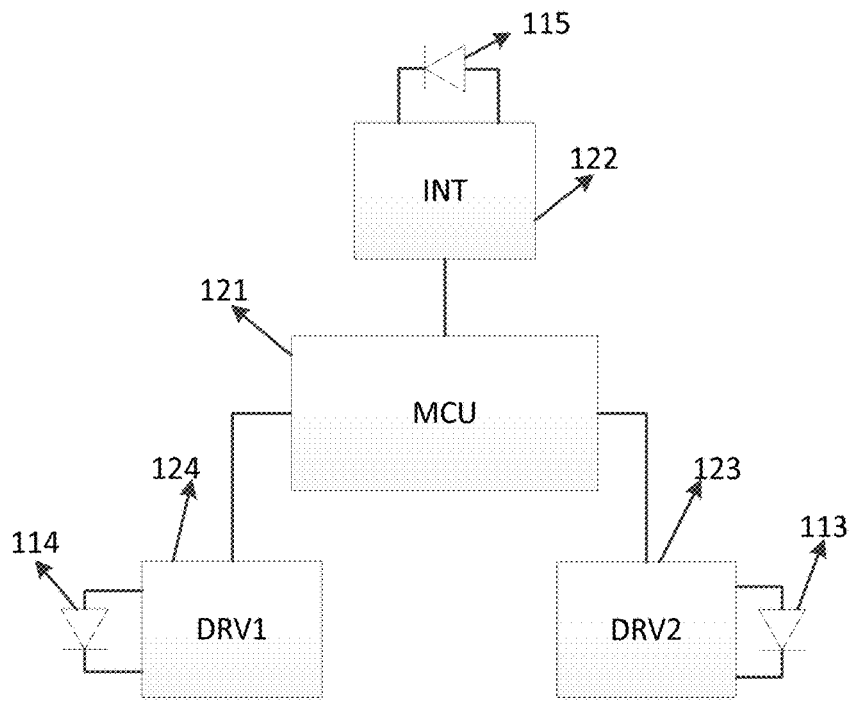
FIG. 4 is a circuit diagram illustrating a detection module according to the first embodiment of the present disclosure.

It is worth mentioning that a circuit structure of a module for implementing a detection function (hereinafter referred to as "a detection module") in a wearable device in this embodiment may be shown as FIG. 4. Specifically, the detection module includes an MCU module 121, an integrator module (an INT module) 122, a driving module (a DRV1 module) 124, a driving module (a DRV2 module) 123, the LED 114 emitting the red light, the LED 113 emitting the green light and the PD 115. In this embodiment, the MCU module 121, as a central processing unit, is mainly configured to process data and control the INT module 122, the DRV1 module 124 and the DRV2 module 123. The INT module 122 is configured to control the light receiver PD 115. The DRV1 module 124 is configured to control the LED 114 emitting the red light, and specifically control brightness and a light emission time of the LED 114. The DRV2 module 123 is configured to control the LED 113 emitting the green light, and specifically control brightness and a light emission time of the LED 113. The MCU control module 121 indirectly controls the LED 114 emitting the red light and the LED 113 emitting the green light by controlling the DRV1 module 124 and the DRV2 module 123, and obtains light signals received by the PD 115 through the INT module 122.

Compared with existing technologies, the wearing state of the wearable device may be detected based on the optical characteristic principle of the human tissue in this embodiment. It may be known from the optical characteristic principle that absorptivities and reflectivities of human tissue to different types of light are different. Therefore, the reflected light of different types of light signals may be different in detected signal intensity in the case of the same distance, and each type of light signal may also change in the signal intensity respectively in the case that the distance changes. Similarly, since absorptivities and reflectivities of human tissue to different types of light are different, the reflected light corresponding to different types of light signals may generate different change trends in the intensity. Compared with a signal intensity absolute value of a certain static point, the change trend of the signal is more interchangeable and interference from an external environment can be reduced, so that the detection result obtained by performing the detection based on this principle is also more accurate. Therefore, specifically, the wearing state of the wearable device may be determined by detecting the change trends of the received reflected light corresponding to at least two types of light signals during a distance change generated by the wearable device and the skin when the wearable device is worn in this embodiment. It may be seen that compared with an existing static detection, the wearing state of the wearable device may be determined more accurately by adopting a dynamic detection, i.e. a dynamically-changing data detection result. In addition, two types of light signals and three wearing states are further defined, and a wearing rule of the wearing state is also defined at the same time, so that the rule of determining each state is clear and simple when the red light and the green light are used for comparison.

It is worth mentioning that although two light emitters are used in the first embodiment, the number of the light emitter y be different, for example, may be one, three, or four or the like in the practical application; meanwhile, although one light receiver is used in this embodiment, more light receivers may be used in the practical application, which is not limited herein.

There are two types of light signals in this embodiment. The wearing state may be determined according to a change trend of a difference value of the reflected light corresponding to the two types of light signals. And the determination may also be performed by using more light signals in the practical application. In a specific determination, a relationship between a change trend of a difference value of two types of reflected light selected from more than two types of light and a pre-stored change trend may be determined, and the wearing state of the wearable device may be determined according to the determination result of the change trend; or all types of reflected light are combined in pairs, a relationship between a change trend of a difference value of each pair of reflected light and a pre-stored change trend may be determined respectively, and the wearing state of the wearable device may be determined according to the determination result of the change trend.

A second embodiment of the present disclosure relates to a method for detecting a wearing state. This embodiment is similar to the first embodiment with a main difference in that: wavelengths of light signals emitted by two light emitters are different in the first embodiment, and distances of two light emitters from a light receiver are different in this embodiment.

Figure 5:
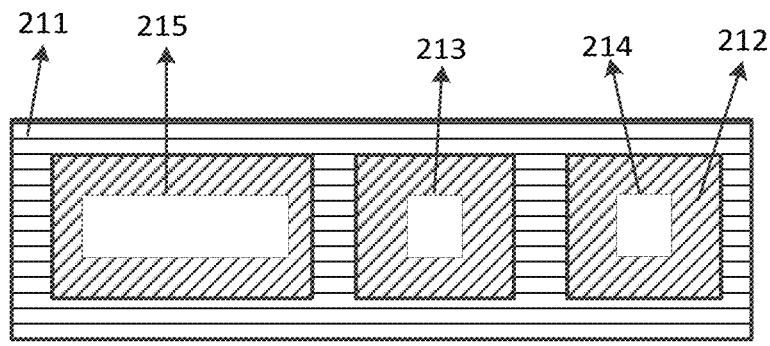
FIG. 5 is a schematic diagram illustrating a detection module according to a second embodiment of the present disclosure.

A structure of a detection module in a wearable device in this embodiment is shown as FIG. 5, which includes: a light isolation component 211, a carrying plate 212, an LED 213, an LED 214 and a PD 215. The light isolation component 211 is mainly configured to isolate a LED light; the carrying plate 212 is mainly configured to carry and fix the LED 213, the LED 214, the PD 215 and the light isolation component 211; the PD 215 is used as a light receiver for receiving light signals.

Figure 6:
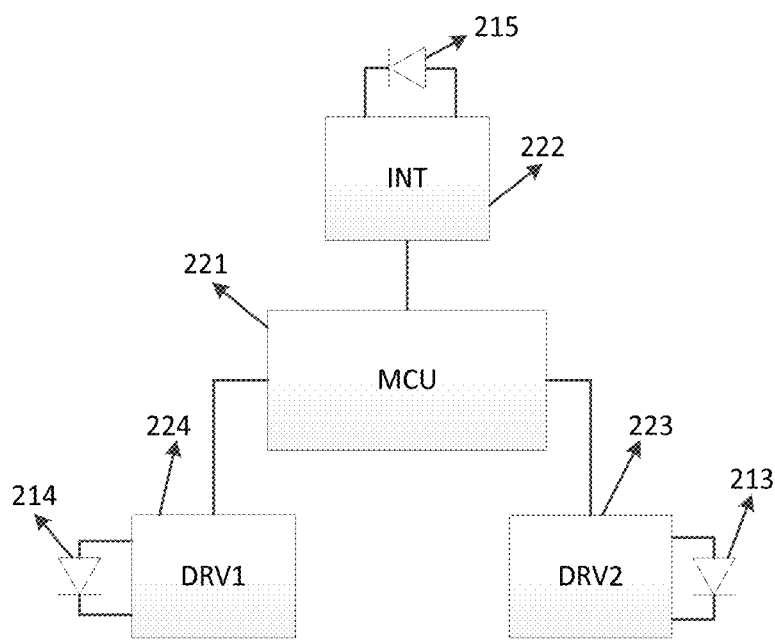
FIG. 6 is a circuit diagram illustrating a detection module according to the second embodiment of the present disclosure.

A circuit structure adopted by a wearing detection solution with the same wavelengths is shown as FIG. 6. The circuit mainly includes a MCU module 221, an INT module 222, a DRV1 module 224, a DRV2 module 223, the LED 214 emitting a red light, the LED 213 emitting a red light and the PD 215. The MCU module 221, as a central processing unit, is mainly configured to process data and control the INT module 222, the DRV1 module 224 and the DRV2 module 223. The INT module 222 is configured to control the light receiver PD 215. The DRV1 module 224 is configured to control the red LED 214, and specifically control brightness and a light emission time of the LED 214. The DRV2 module 223 is configured to control the red LED 213, and specifically control brightness and a light emission time of the LED 213. In addition, the MCU control module 221 indirectly controls the LED 214 emitting the red light and the LED 213 emitting the red light by controlling the DRV1 module 224 and the DRV2 module 223, and obtains light signals received by the PD 215 through the INT module 222.

It may be known from the above description that two LEDs emitting the red light (LED 213 and LED 214) are used as light emitters in this embodiment and distances of the two LEDs from the PD 215 are different. It may be seen from FIG. 5 that the LED 213 is closer to the PD 215. Therefore, since distances of the LED 213 and the LED 214 from the PD 215 are different, when a distance between a human skin tissue and the wearable device changes, transmission paths of light emitted by two LEDs change, and change trends of reflected light received by the PD 215 may also be different. The distance between the wearable device and the skin may be determined according to the two types of received reflected light and thus is taken as a basis of determining an attaching state of the wearable device and the skin. When signal amounts of the two types of received reflected light change, the change trend of the distance between the wearable device and the skin may be determined according to the change trends of the signal amounts of the two types of reflected light, thereby performing a dynamic detection of wearing and falling-off states.

It is to be noted that a time division detection method may be adopted in this embodiment. Specifically, one detection period is divided into several emission stages, and the number of emission stages included in each transmission period is the same with the type number of light signals. Controlling the light emitter to emit at least two types of light signals to a user according to the preset emission period includes: controlling the light emitter to emit one type of light signal to the user in each emission stage according to the preset emission period.

Figure 7:
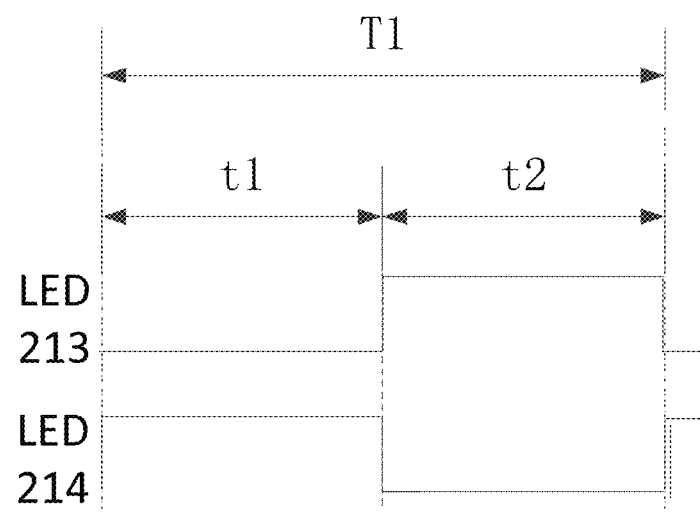
FIG. 7 is a schematic diagram illustrating an operation time sequence in a method of detecting a wearing state according to the second embodiment of the present disclosure.

Specifically, an operation time sequence diagram this embodiment may be shown as FIG. 7, FIG. 7 shows one period T in which a system operates. One operation period T1 is divided into two stages t1 and t2. In the stage t1, the LED 213 emitting the red light emits light, and the LED 214 emitting the red light does not emit light. In the stage t2, the LED 213 emitting the red light does not emit light, and the LED 214 emitting the red light emits light. Meanwhile, in the whole period T, the PD 215 is always in an operating state, that is, the PD 215 receives a light signal of the LED 213 emitting the red light in the stage t1, and receives a light signal of the LED 214 emitting the red light in the stage t2. Then, the PD 215 sends the received light signals to the MCU module 221 for processing. The stages t1 and t2 may be half a period respectively, i.e., ½T1. That is, if T1 is 100 microseconds, t1 and t2 may be 50 microseconds respectively.

It may be seen in this embodiment that the change trends of the received light are different due to different distances of the light emitters from the light receiver, thereby realizing the detection of the wearing state of the wearable device. The wearing state of the wearable device is detected by a method that is provided by this embodiment and the method differs from the method provided by the first embodiment, so that the present disclosure may be applied to different application scenarios, and different implementation solutions may be selected in a practical application according to an actual situation. In addition, a time division operation method is also added in this embodiment, by which two light emitters are set to be in different operation time sequences, so that two types of light signals do not interfere with each other, thereby reducing a wrong determination.

In addition, it is to be noted that the technical solution mentioned in the first embodiment may also be combined with the technical solution mentioned in this embodiment at the same time in a practical application, that is, not only wavelengths of the adopted two LEDs are different, but also distances of the adopted two LEDs from the light receiver are different.

A third embodiment of the present disclosure relates to a method for detecting a wearing state. This embodiment is similar to the first embodiment with a main difference in that: one light receiver is adopted in the first embodiment, but two light receivers are adopted in this embodiment.

Figure 8:
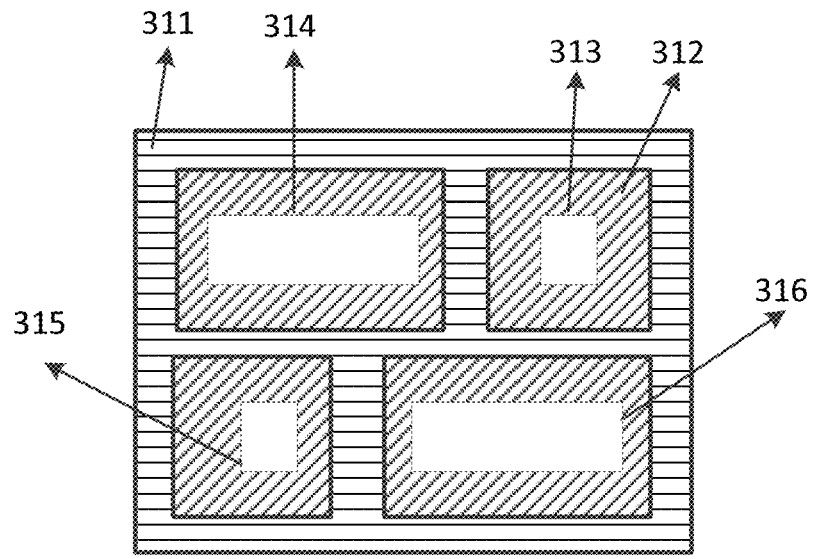
FIG. 8 is a schematic diagram illustrating a detection module according to a third embodiment of the present disclosure.

Specifically, a detection module in this embodiment may be shown as FIG. 8, which includes: a light isolation component 311, a carrying plate 312, a LED 313 emitting a red light, a LED 315 emitting a green light, a PD 314 and a PD 316. The light isolation component 311 is mainly configured to isolate a LED light; the carrying plate 312 is mainly configured to carry and fix the LED 313 emitting the red light, the LED 315 emitting the green light, the PD 314, the PD 316 and the light isolation component 311; the LED 313 emitting the red light and the LED 315 emitting the green light are used as light emitters for emitting the red light and the green light respectively; the PD 314 and the PD 316 are used as light receivers.

Figure 9:
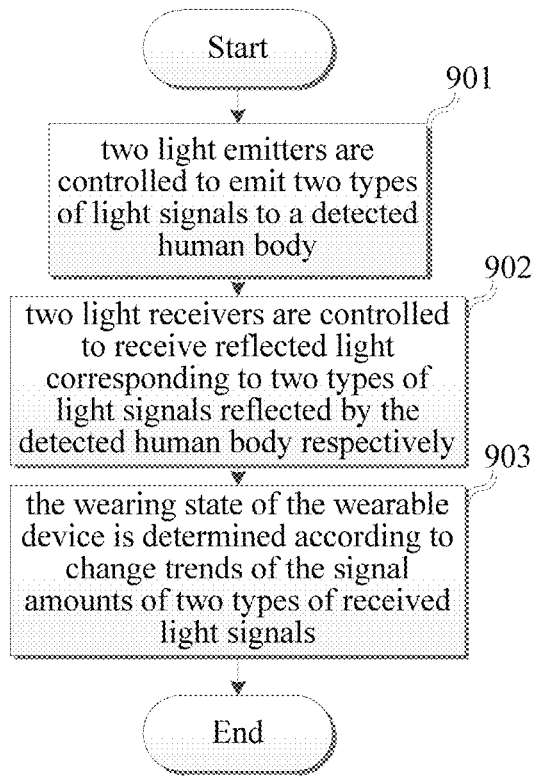
FIG. 9 is a flowchart illustrating a method for detecting a wearing state according to the third embodiment of the present disclosure.

The method for detecting the wearing state in this embodiment is shown as FIG. 9, which includes the following steps.

Step 901 in this embodiment is similar to step 201 in the first embodiment, which is not described herein.

At step 902, two light receivers are controlled to receive two types of reflected light corresponding to two types of light signals reflected by a user respectively.

Specifically, different light receivers receive different light signals. In this embodiment, the PD 314 is only sensitive to the red light and thus only receives a red-light signal, and the PD 316 is only sensitive to the green light and thus only receives a green-light signal.

Step 903 in this embodiment is similar to step 203 in the first embodiment, which is not described herein.

Figure 10:
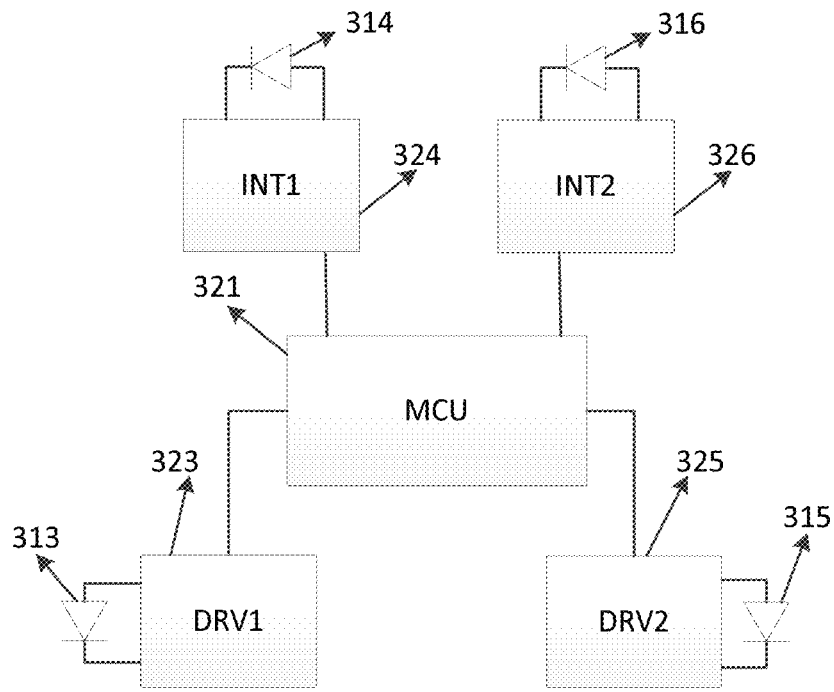
FIG. 10 is a circuit diagram illustrating a detection module according to the third embodiment of the present disclosure.

A circuit of a detection module in this embodiment may be shown as FIG. 10, which mainly includes a MCU module 321, an INT1 module 324, an INT2 module 326, a DRV1 module 323, a DRV2 module 325, the LED 313 emitting the red light, the LED 315 emitting the green light, the PD 314 and the PD 316. The MCU module 321, as a central processing unit, is mainly configured to process data and control the INT1 module 324, the INT2 module 326, the DRV1 module 323 and the DRV2 module 325. The INT1 module 324 is configured to control the light receiver PD 314, and the INT2 module 326 is configured to control the light receiver PD 316. The DRV1 module 323 is configured to control the LED 313 emitting the red light, and specifically configured to control brightness and a light emission time of the LED 214. The DRV2 module 325 is configured to control the LED 315 emitting the green light, and specifically configured to control brightness and a light emission time of the LED 315. The MCU control module 321 indirectly controls the LED 313 emitting the red light and the LED 315 emitting the green light by controlling the DRV1 module 323 and the DRV2 module 325, obtains the red-light signal received by the PD 314 through the INT1 module 324, and obtains the green-light signal received by the PD 316 through the INT2 module 326.

It may be seen in this embodiment that since reflectivities and refractivities of skin tissue to the red light and the green light are different, the light signals received by the PD 314 and the PD 316 are different when distances of the skin from the detection module are different, so that the wearing state may be indirectly determined by determining the distance of the detection module and the skin according to a difference value of two types of light signals. When the distance of the skin and the detection module changes, transmission paths of light emitted by two LEDs change. The distance of the detection module and the skin may be determined according to signal amounts of the received two light signals, and thus is taken as a basis of determining an attaching state of the detection module and the skin. When the signal amounts of two types of the received reflected light change, a change trend of the distance of the detection module and the skin may be determined according to change trends of the light signal amounts of two types of the received reflected light, thereby performing a dynamic detection of wearing and falling-off states.

It is worth mentioning that although two light receivers are adopted in this embodiment, more light receivers may be used in a practical application. Particularly, when there are more light emitters, more light receivers may be adopted. For embodiment, each light emitter is provided corresponding to each light receiver respectively, so that the specific number of light receivers is not limited herein.

A fourth embodiment of the present disclosure relates to a method for detecting a wearing state. This embodiment is further improved based on the first embodiment, with a main improvement in that: an acceleration sensor (i.e., Gsensor) is added to perform a determination in combination with signal amounts received by a light receiver in this embodiment, so that a detection result is more accurate.

Figure 11:
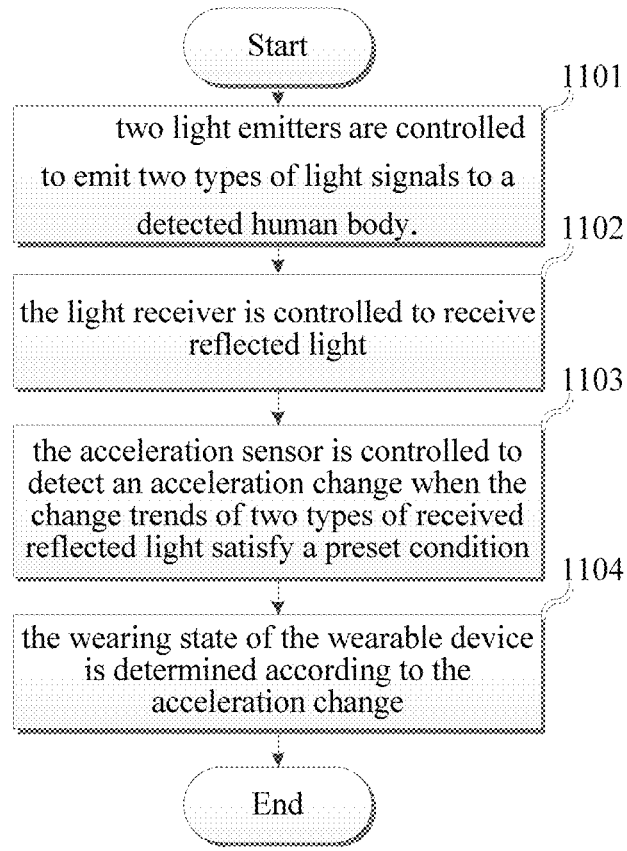
FIG. 11 is a flowchart illustrating a method for detecting a wearing state according to a fourth embodiment of the present disclosure.

Specifically, the method for detecting the wearing state in this embodiment is shown as FIG. 11, which includes the following steps.

Steps 1101 and 1102 in this embodiment are similar to steps 201 and 202 in the first embodiment, which are not described herein.

At step 1103, when change trends of two types of received reflected light satisfy a preset condition, the acceleration sensor is controlled to detect an acceleration change.

Specifically, the preset condition may be that the change trends presented by two types of the reflected light when the wearing state is "being worn" or "well worn" are satisfied, which may be specifically set by a technician according to simulation data or experience.

At step 1104, the wearing state of the wearable device is determined according to the acceleration change.

Specifically, the inventor of the present disclosure found that the acceleration change may exist when the wearable device is well worn. Thus, when a signal amount change satisfies the preset condition, the acceleration change may be determined to more accurately determine whether the wearable device is well worn, thereby reducing a wrong determination rate. That is, the wearing state of the wearable device may be determined according to the change trends of two types of the received reflected light and the acceleration change detected by the acceleration sensor.

In addition, although a first determination may be performed for the change trend of the reflected light in this embodiment, a first determination may also be performed by the acceleration sensor in a practical application, or both determinations may be performed at the same time.

Specifically, after the change trend of the reflected light is detected, the acceleration change may be detected by the Gsesnor in this embodiment. When the wearable device is worn, the wearable device may generate an acceleration change. Thus, accuracy of the detection result may be greatly increased by adding the detection by the Gsensor. It is noted that the change trend of the reflected light are firstly determined and the detection by the Gsensor is then performed in this embodiment. However, in the practical application, the detection by the Gsensor may also be firstly determined, and then, the detection of the change trend of the reflected light may be started when the acceleration change detected by the Gsensor satisfies the preset condition.

In addition, the detection by the Gsensor and the detection of the change trend of the reflected light may be combined in this embodiment. In the practical application, a heart rate signal may also be detected by PhotoPlethysmoGraphy (PPG), thereby determining the wearing state by combining the detection of the heart rate signal with the detection of the change trend of the reflected light. Since the wearable device is very close to a human tissue after being correctly worn, physiological signals such as a heart rate, a blood pressure and blood oxygen may be detected. Therefore, the accuracy of the detection result may also be greatly improved by performing the detection combined with the PPG. For embodiment, the detection of the change trend of the reflected light is firstly performed. If the detection result is "well worn", the detection by PPG may be further performed. When the PPG detects the heart rate signal, the detection result is output as "well worn", thereby effectively reducing the wrong determination rate. Meanwhile, when the detection result is another wearing state such as "not worn", a heart rate detection function is not required to start, thereby reducing a running time of the heart rate detection and effectively lowering a power consumption of the detection module.

Further, in the practical application, the detections of the acceleration change and the heart rate may be combined with the detection of the change trend of the reflected light at the same time to further improve the accuracy of the detection result.

A fifth embodiment of the present disclosure relates to a method for detecting a wearing state. This embodiment is similar to the first embodiment with a main difference in that: the wearing state is determined by combining a comparison result of a difference value of the reflected light and a specific threshold with change trend of the difference value in the first embodiment, and the wearing state is determined according to a particular feature partition of a pre-stored feature curve to which a curve formed by the difference value belongs in this embodiment. Since details of the change trend may more easily remain in the curve, the wearing state determined by comparing the curves is more accurate.

Figure 12:
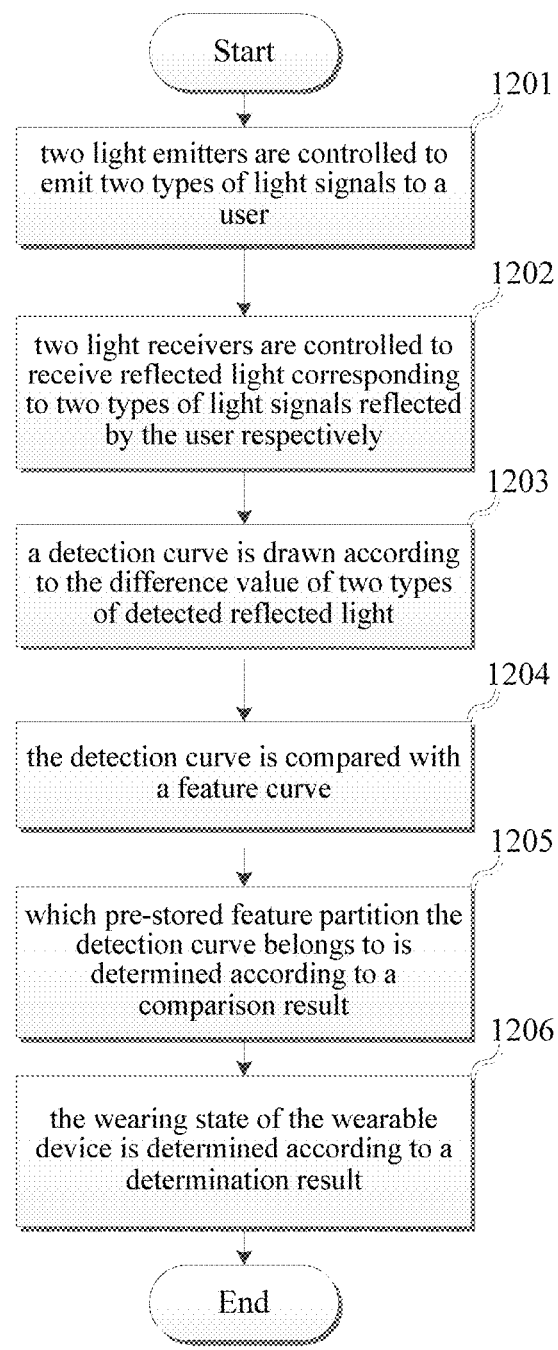
FIG. 12 is a flowchart illustrating a method for detecting a wearing state according to a fifth embodiment of the present disclosure.

A flowchart of a detection method in this embodiment is shown as FIG. 12, which includes the following steps.

Steps 1201 and 1202 in this embodiment are similar to steps 201 and 202 in the first embodiment, which are not described herein.

At step 1203, a detection curve is drawn according to the difference value of two types of the detected reflected light.

Figure 13A:
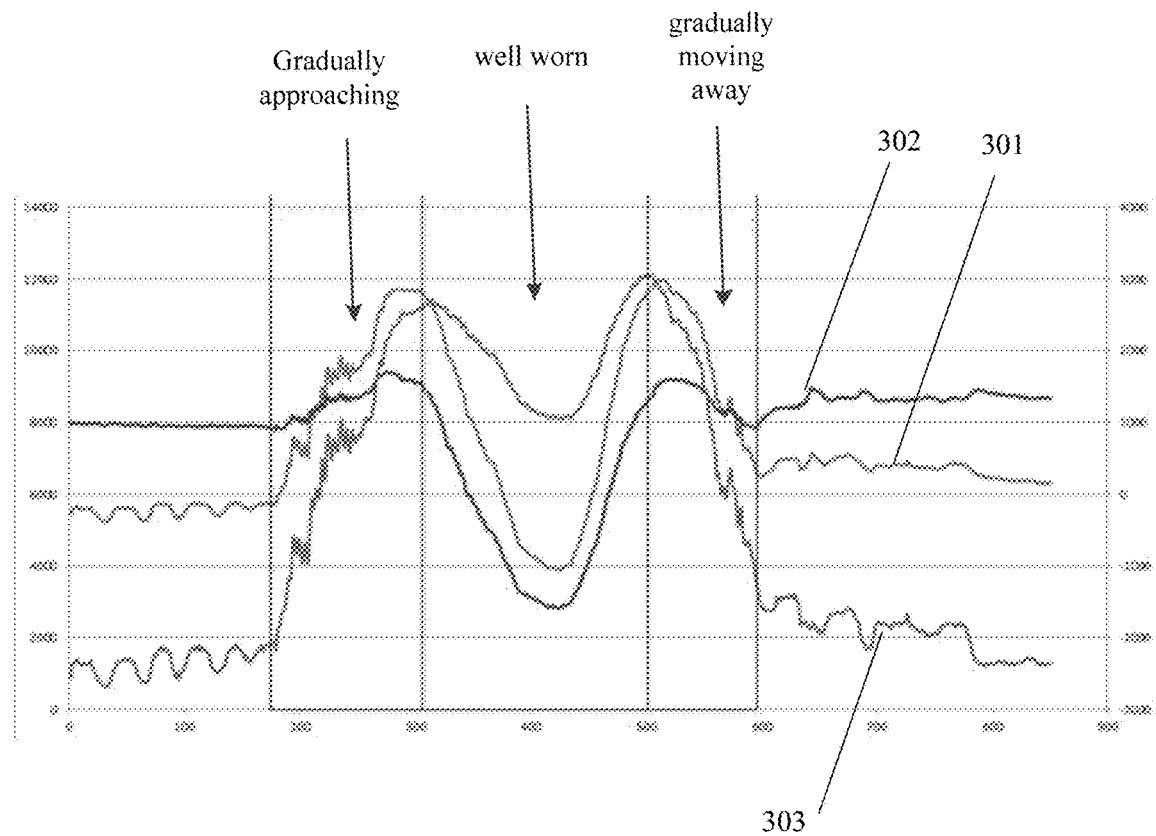
FIG. 13a is a schematic diagram illustrating drawing a detection curve in a method for detecting a wearing state according to the fifth embodiment of the present disclosure.

Specifically, the detection curve may be drawn according to the difference value of the two types of the reflected light detected in the last 100 detection periods in this embodiment. Since each difference value is obtained corresponding to each detection period respectively, one detection curve may be obtained by performing curve fitting based cm data of the last 100 difference values. A schematic diagram of the detection curve is shown as FIG. 13a. In FIG. 13a, a curve 301 is a curve of a signal amount of the reflected light corresponding to a green light, a curve 302 is a curve of a signal amount of the reflected light corresponding to a red light, and a curve 303 is a detection curve obtained by subtracting the signal amount of the reflected light corresponding to the red light from the signal amount of the reflected light corresponding to the green light.

At step 1204, the detection curve is compared with the feature curve.

Figure 13B:
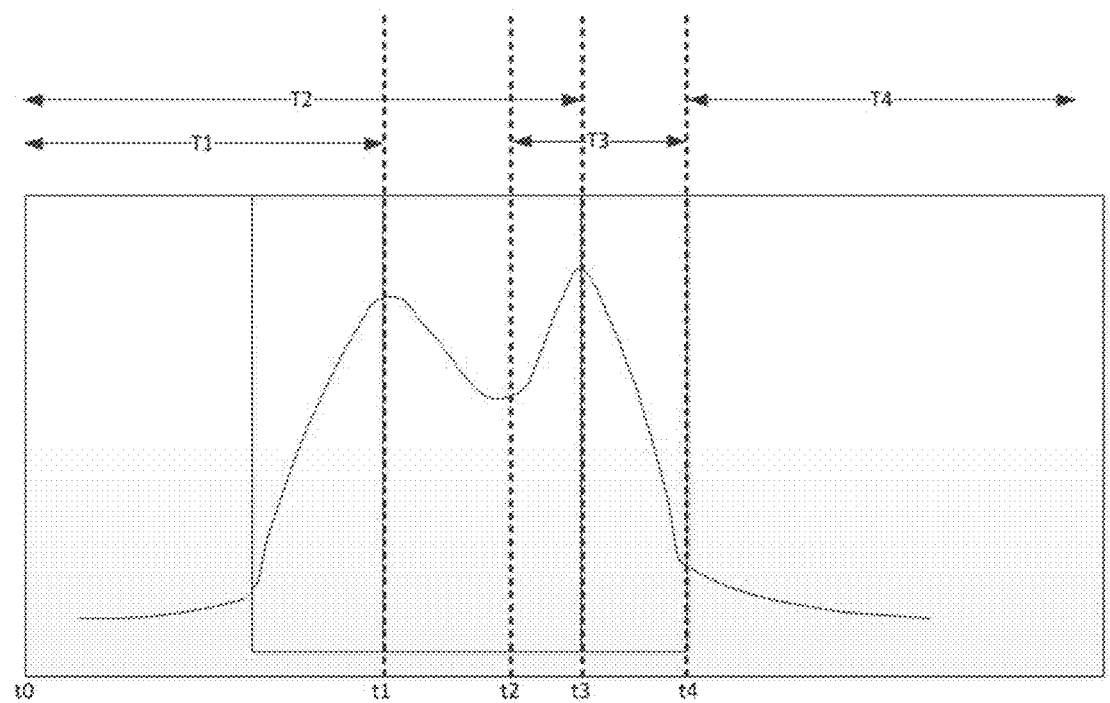
FIG. 13b is a schematic diagram illustrating a feature curve in a method for detecting a wearing state according to the fifth embodiment of the present disclosure.

Specifically, the detection curve is the detection curve obtained at step 1203, and the feature curve may be predrawn by a designer according to a wavelength of a used light signal and may include several feature partitions. The feature curve and a division manner of the feature curve shown as FIG. 13b may be adopted in this embodiment, where t0-t1 are divided as a feature partition T1, t0-t3 are divided as a feature partition T2, t2-t4 are divided as a feature partition T3, and t4—are divided as a feature partition T4 according to a time sequence.

More specifically, matching may be performed in a curve fitting manner (or another manner) during a comparison, and a configuration index is represented by a fitting degree R square value (or another index), for embodiment, the R square value may be 0.8 or another value, which is not limited herein.

In addition, it is to be noted that not all curves in the whole feature partition are required to fit during curve fitting, and one matching parameter X may be added, where X refers to a portion in which the detection curve and the pre-stored curve are successfully fitted. For embodiment, when the partition T2 is fitted, the fitting may be performed in t0-tx (tx is between t1 and t2), for embodiment, the portion of t0-t1 accounts for 60% of the whole T2 (the corresponding x is 0.6), and the portion of t0-t2 accounts for 80% of the whole T2 (the corresponding x is 0.8). When the detection curve can be successfully matched with the portion of t0-tx (tx is between t1 and t2) (the R square value is greater than 0.8), the X value is between 0.6 and 0.8.

At step 1205, which the pre-stored feature partition the detection curve belongs to is determined according to a comparison result.

Specifically, different feature curves may be compared one by one according to the time sequence of the feature curves.

For embodiment, the detection curve is firstly compared with the curve in the partition T1. When the comparison result reaches 0.8, it is determined that the detection curve belongs to the feature partition T1. When the comparison result does not reach 0.8, the comparison is continued, and the detection curve may also be deformed firstly and then compared with the feature curve in the partition T1 at the same time. If the comparison result still does not reach 0.8 after a period of time, it is determined as "unsuccessfully worn", and a return is made to the step of drawing the detection curve. In this stage, once it is determined that the detection curve belongs to the feature partition T1, the comparison with the feature partition T2 is continued. The method for comparing with the feature partition T2 is similar to the method for comparing with the feature partition T1. It is to be noted that if the feature partition T2 still cannot be matched after a period of time, a return is made to compare with the feature partition T1 again.

It is worth mentioning that an above-mentioned curve deformation may refer to that the drawn detection curve is transversely stretched or compressed to remove a possible wearing speed difference during a use by the user, or the detection curve may be partially stretched or compressed. The curve stretched or compressed in this way is much easier to be matched with the feature curves.

Descriptions are continued here: after it is determined that the detection curve belongs to the feature partition T2, the drawing of the detection curve is continued with new detection data. Meanwhile, the detection curve at this time may be compared with the feature curve in the partition T3, and a determination herein may be continued without a time upper limit. After it is determined that the detection curve belongs to the partition T3, the detection curve is further compared with the feature curve in the partition 14. After it is determined that the detection curve belongs to the partition 14, the curve drawn thereafter is compared with the curve T1 again, and so on.

At step 1206, the wearing state of the wearable device is determined according to a determination result.

Specifically, if the determination result is that the detection curve belongs to the feature partition T1, the wearing state is determined as "gradually approaching"; if the determination result is that the detection curve belongs to the feature partition T2, the wearing state is determined as "well worn", if the determination result is that the detection curve belongs to the feature partition T3, the wearing state is determined as "gradually moving away"; if the determination result is that the detection curve belongs to the feature partition T4, the wearing state is determined as "unsuccessfully worn".

As can be seen, it is defined in this embodiment that the change trend of the difference value of two types of the reflected light is determined according to a feature curve diagram and the divided feature partitions. The wearing state may be obtained more accurately by using the detection curve, and a richer determination method is provided at the same time. In addition, since the wearable device may not be taken off shortly after being worn, when the partition T3 is determined, no time upper limit is set, which can be applied in an actual application scenario, thereby obtaining the more accurate determination result.

A sixth embodiment of the present disclosure relates to a method for detecting a wearing state. This embodiment is further improved based on the first embodiment with a main improvement in that: an emission period is divided into two emission stages, and one type of light signal is emitted to a user in each emission stage. Thus, different types of light signals can be sent based on a time division emission mechanism, thereby reducing interference between the light signals when the light signals are received.

In the method for detecting the wearing state in this embodiment, each emission period is divided into several emission stages, and the number of emission stages included in each emission period is the same with the type number of the light signals. Controlling light emitter to emit at least two types of the light signals to the user according to the preset emission period includes: controlling the light emitter to emit one type of light signal to the user in each emission stage according to the preset emission period.

Figure 14:
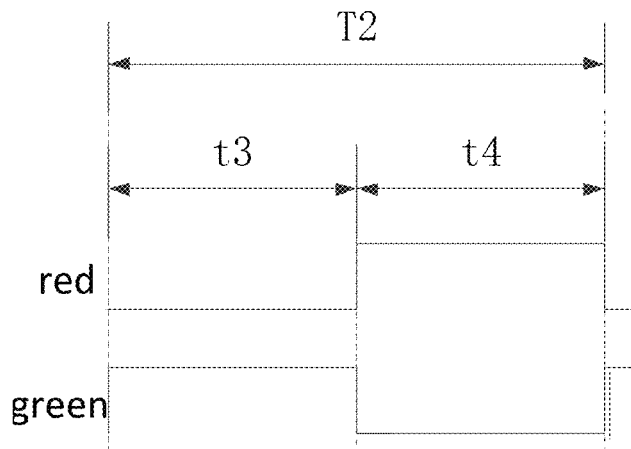
FIG. 14 is a schematic diagram illustrating an operation time sequence in a method for detecting a wearing state according to a sixth embodiment of the present disclosure.

A time sequence diagram for detecting the wearing state in embodiment is shown as FIG. 14. FIG. 14 shows one period T2 in which a system operates. One operation period T2 is divided into two stages t3 and t4, where t3 corresponds to a LED emitting a green light, and t4 corresponds to a LED emitting a red light. Therefore, in the stage t3, the LED emitting the green light emits light, and the LED emitting the red light does not emit light; in the stage t4, the LED emitting the green light does not emit light, and the LED emitting the red light emits light. Meanwhile, in the whole period T, a light receiver is always in an operating state. That is, the light receiver receives a light signal of the LED emitting the green light in the stage t3, and receives a light signal of the LED emitting the red light in the stage t4. After that, the light signals received by the PD are processed.

It may be seen that the light signals are emitted in a time division manner in this embodiment, so that the interference between two types of the light signals can be reduced and the detection result is more accurate.

A seventh embodiment of the present disclosure further relates to a method for detecting a wearing state. This embodiment is further improved based on the first embodiment, with a main improvement in that: a state flag is added to perform a joint determination with the state flag and light signal amounts. In this way, a determination result is more accurate.

Specifically, the state flag s updated every time the wearing state is determined. When the wearing state of the wearable device is determined according to a relationship between a difference value and two preset first signal amount thresholds, the wearing state of the wearable device may be determined according to the relationship between the difference value and the two preset first signal amount thresholds and the state flag.

The inventor found that, when the wearing state is "being worn", the wearing state may be further divided into "gradually approaching" and "gradually moving away". When the state flag is determined, the state of "being worn" can be sub-divided according to change trend of light. For embodiment, when the state flag is "well worn", the wearing state may be determined as "gradually moving away" in combination with a characteristic that light signal amount continuously decreases; when the state flag is "falling off", the wearing state may be determined as "gradually approaching" in combination with a characteristic that the light signal amount continuously increases.

The detection method in this embodiment further includes: presetting the state flag for the wearable device. Determining the wearing state of the wearable device according to the relationship between the difference value and the two preset first signal amount thresholds includes: determining the wearing state of the wearable device according to the relationship between the difference value and the two preset first signal amount thresholds and the state flag.

It may be further optimized that updating the state flag according to the determined wearing state is further included after the wearing state of the wearable device is determined according to the relationship between the difference value and the two preset first signal amount thresholds.

It is further defined in this embodiment that the wearable device is provided with a state flag indicating a current state of the wearable device. During the determination, the joint determination may be performed in combination with the current state, so that the determination result of the wearing state is more accurate.

The steps of different methods above are divided for clarity of description. During implementation, the steps may be combined into one step or some steps may be divided into a plurality of steps. As long as a same logical relationship is included, the steps shall all fall into a scope of protection of the present disclosure. All insignificant modifications or designs that are added or introduced to algorithms or processes without changing a core design of the algorithms or the processes shall all fall into the scope of protection of the present disclosure.

An eighth embodiment of the present disclosure relates to a detection module.

Figure 15:
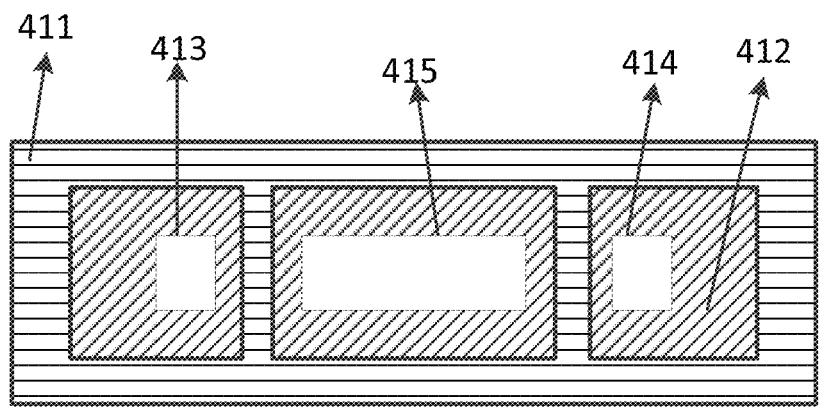
FIG. 15 is a schematic diagram illustrating a detection module according to an eighth embodiment of the present disclosure.

The detection module in this embodiment may be applied to a wearable device and may be shown as FIG. 15. The detection module includes two light emitters (a LED 413 and a LED 414), one light receiver (a PD 415) and a processor (i.e., a MCU). The processor is configured to control the light emitters to emit two types of light signals to a user, control the light receiver to receive reflected light corresponding to the two types of light signals reflected by the user, and determine a wearing state of a wearable device according to change trends of the two types of reflected light received by the light receiver.

Specifically, the change trend of the reflected light in this embodiment may be represented by following parameters: light intensity, light brightness or light illuminance. More specifically, one of the above parameters or a plurality of the above parameters may be used.

It is to be noted that the detection module in this embodiment further includes: a light isolation component 411 and a carrying plate 412. The light isolation component 411 is mainly configured to isolate a LED light, and the carrying plate 412 is mainly configured to carry and fix the LED 413, the LED 414, the PD 415 and the light isolation component 411.

In addition, wavelengths of the light signals emitted by at least two light emitters are different, or distances of at least two light emitters from the light receiver are different in this embodiment. In a practical application, the wavelengths of light signals emitted by the two light emitters are different and the distances of the two light emitters from the light receiver are also different at the same time. In addition, there may also be at least two light receivers in the practical application. It is to be noted that this embodiment is an apparatus embodiment corresponding to the first embodiment, and this embodiment and the first embodiment may be implemented in cooperation with each other. Related technical details mentioned in the first embodiment are still effective in this embodiment, which will not be described herein to reduce repetition. Correspondingly, related technical details mentioned in this embodiment may also be applied to the first embodiment.

A ninth embodiment of the present disclosure relates to a detection module. This embodiment is further improved based on the sixth embodiment, with a main improvement in that: the detection module further includes an acceleration sensor connected with a processor, and the processor is further configured to determine a wearing state of a wearable device according to change trends of at least two types of received reflected light and a value detected by the acceleration sensor.

This embodiment is an apparatus embodiment corresponding to the fourth embodiment, and this embodiment and the fourth embodiment may be implemented in cooperation with each other. Related technical details mentioned in the fourth embodiment are still effective in this embodiment which will not be described herein to reduce repetition. Correspondingly, related technical details mentioned in this embodiment may also be applied to the fourth embodiment.

A tenth embodiment of the present disclosure relates to a wearable device, including: a detection module as mentioned in the eighth embodiment or the ninth embodiment.

Figure 16:
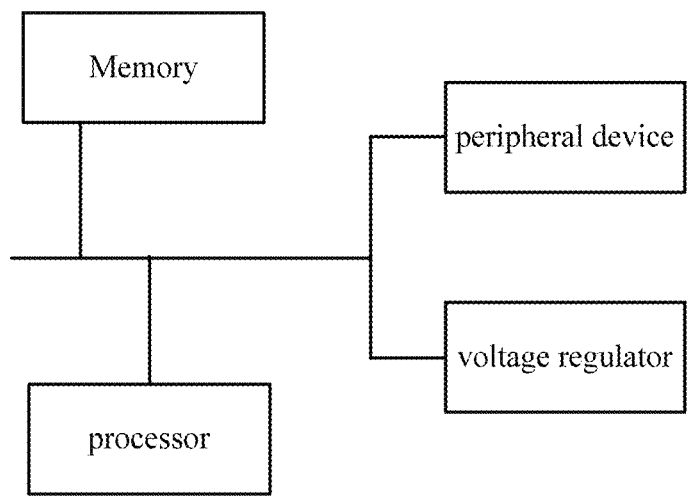
FIG. 16 is a schematic diagram illustrating a wearable device according to an eleventh embodiment of the present disclosure.

An eleventh embodiment of the present disclosure further relates to a wearable device as shown in FIG. 16, including:
at least one processor; and a memory connected and communicated with the at least one processor, where the memory stores instructions executable by the at least one processor, and the instructions are executed by the at least one processor to enable the at least one processor to perform any method for detecting a wearing state as mentioned in the first to seventh embodiments.

The memory and the processor are connected via a bus, the bus may include any number of interconnected buses and bridges, and connect different circuits of one or more processors and memories together. The bus may also connect other different circuits together, such as peripheral devices, voltage regulators and power management circuits, which are known in existing technologies and will not be further described herein. A bus interface provides an interface between the bus and a transceiver. The transceiver may be an element or a plurality of elements, such as a plurality of receivers and transmitters, which provide units for communicating with other apparatuses on a transmission medium. Data processed by the processor is transmitted on a wireless medium via an antenna. Further, the antenna also receives data and transmits the data to the processor.

The processor is used for bus management and normal processing, and may provide different functions including timing, peripheral interfaces, voltage regulation, power management and other control functions. The memory may be configured to store data used when the processor performs an operation.

A twelfth embodiment of the present disclosure relates to a non-transitory storage medium having computer-readable instructions, where the computer-readable instructions are executed by at least one processor to perform any method for detecting a wearing state in the first to seventh embodiments.

Persons skilled in the art may understand that implementation of all or some of steps in the methods of the above embodiments may be completed by instructing related hardware via a program. The program is stored in one storage medium, and includes several instructions for enabling one apparatus (such as a single chip computer and a chip) or processor to perform all or some of the steps of the methods in different embodiments of the present disclosure. The above storage medium includes: a USB flash disk, a mobile hard disk, a Read-Only Memory (ROM), a Random Access Memory (RAM), a magnetic disc or a compact disk and the like which may store program codes.

Persons of ordinary skill in the art may understand that the above embodiments are specific embodiments for implementing the present disclosure. In a practical application, various changes in form and detail may be made to the embodiments without departing from the spirit and the scope of the present disclosure.

What is claimed is:

1. A method for detecting a wearing state, applicable to a wearable device, wherein the wearable device comprises a light emitter and a light receiver; the method comprises:
controlling the light emitter to emit two types of light signals to a user of the wearable device; wherein the two types of light signals are a red light and a green light respectively;
controlling the light receiver to receive reflected light corresponding to the two types of light signals reflected by the user; and
determining the wearing state of the wearable device according to change trends of the two types of the received reflected light; the wearing state is divided into three levels, and a higher level corresponds to better wearing quality;
wherein,
the determining the wearing state of the wearable device according to the change trends of the two types of the received reflected light comprises:
determining a relationship between a difference value of the two types of the reflected light and two preset first signal amount thresholds; the difference value is equal to a signal amount of reflected light corresponding to the green light minus a signal amount of reflected light corresponding to the red light the two preset first signal amount thresholds are a first threshold and a second threshold respectively, wherein the first threshold is greater than the second threshold; and
determining the wearing state of the wearable device according to a determination result of the relationship; wherein
when the difference value is greater than or equal to the first threshold, further determining the change trend of the difference value; determining the wearing state as a third-level wearing state when the difference value continuously increases; returning to determine the relationship between the difference value and the first threshold when the difference value continuously decreases or is unchanged;

when the difference value is greater than the second threshold and less than the first threshold, further determining the change trend of the difference value; determining the wearing state as a second-level wearing state when the difference value is unchanged or decreases; returning to determine the relationship between the difference value and the second threshold when the difference value continuously increases; and when the difference value is less than or equal to the second threshold, determining the wearing state as a first-level wearing state.

2. The method according to claim 1, wherein, the change trend of the reflected light is represented by at least one of following parameters: light intensity, light brightness, and light illuminance.

3. The method according to claim 1, wherein,
the method further comprises: presetting a state flag for the wearable device;
determining the wearing state of the wearable device according to the relationship between the difference value and the two preset first signal amount thresholds comprises: determining the wearing state of the wearable device according to the relationship between the difference value and the two preset first signal amount thresholds and the state flag.

4. The method according to claim 3, wherein,
after the wearing state of the wearable device is determined according to the relationship between the difference value and the two preset first signal amount thresholds, the method further comprises: updating the state flag according to the determined wearing state.

5. The method according to claim 1, wherein,
controlling the light emitter to emit at least two types of light signals comprises: controlling at least two light emitters to emit the at least two types of light signals, wherein distances of the at least two light emitters from the light receiver are different.

6. The method according to claim 1, wherein,
controlling the light emitter to emit two types of light signals to the user comprises: controlling the light emitter to emit two types of light signals to the user according to a preset emission period, wherein each emission period is divided into two emission stages;
controlling the light emitter to emit two types of light signals to the user according to the preset emission period comprises:
controlling the light emitter to emit one of the two types of light signals to the user in one of the two emission stages and to emit another of the two types of light signals to the user in another of the two emission stages, according to the preset emission period.

7. The method according to claim 1, wherein,
the wearable device further comprises an acceleration sensor;
before the light receiver is controlled to receive the reflected light corresponding to two types of light signals reflected by the user, the method further comprises:
controlling the acceleration sensor to detect an acceleration change;

determining the wearing state of the wearable device according to the change trends of two types of the received reflected light comprises:
determining the wearing state of the wearable device according to the change trends of two types of the received reflected light and the acceleration change detected by the acceleration sensor.

8. The method according to claim 1, wherein,
before the step of determining the wearing state of the wearable device according to the change trends of two types of the received reflected light is performed, the method further comprises: detecting a heart rate signal of the user;
determining the wearing state of the wearable device according to the change trends of two types of the received reflected light comprises:
determining the wearing state of the wearable device according to the change trends of two types of the received reflected light and a detection result of the heart rate signal.

9. A module for detecting a wearing state, wherein the module is applicable to a wearable device and comprises a light emitter, a light receiver and a processor;
wherein the processor is electrically connected with the light emitter and the light receiver respectively;
and the processor is configured to control the light emitter to emit two types of light signals to a user, control the light receiver to receive reflected light corresponding to two types of light signals reflected by the user, and determine the wearing state of the wearable device according to change trends of the two types of the reflected light received by the light receiver; wherein the processor is further configured to:
determine a relationship between a difference value of the two types of the reflected light and two preset first signal amount thresholds; and
determine the wearing state of the wearable device according to a determination result of the relationship; wherein
the two types of light signals are a red light and a green light respectively;
the wearing state is divided into three levels, and a higher level corresponds to better wearing quality;
the difference value is equal to a signal amount of reflected light corresponding to the green light minus a signal amount of reflected light corresponding to the red light;
the two preset first signal amount thresholds are a first threshold and a second threshold respectively, wherein the first threshold is greater than the second threshold;
when the difference value is greater than or equal to the first threshold, further determining the change trend of the difference value; determining the wearing state as a third-level wearing state when the difference value continuously increases; returning to determine the relationship between the difference value and the first threshold when the difference value continuously decreases or is unchanged;
when the difference value is greater than the second threshold and less than the first threshold, further determining the change trend of the difference value; determining the wearing state as a second-level wearing state when the difference value is unchanged or decreases; returning to determine the relationship between the difference value and the second threshold when the difference value continuously increases; and when the difference value is less than or equal to the second threshold, determining the wearing state as a first-level wearing state.

10. The module according to claim 9, wherein, the module further comprises an acceleration sensor connected with the processor;

wherein the processor is further configured to determine the wearing state of the wearable device according to the change trends of two types of the received reflected light and a value detected by the acceleration sensor.

11. A wearable device, characterized by comprising a module for detecting a wearing state, wherein the module comprises a light emitter, a light receiver and a processor;

wherein the processor is electrically connected with the light emitter and the light receiver respectively;

and the processor is configured to control the light emitter to emit two types of light signals to a user, control the light receiver to receive reflected light corresponding to two types of light signals reflected by the user, and determine the wearing state of the wearable device according to change trends of the two types of the reflected light received by the light receiver; wherein, the processor is further configured to:

determine a relationship between a difference value of the two types of the reflected light and two preset first signal amount thresholds; and determine the wearing state of the wearable device according to a determination result of the relationship; wherein, the two types of light signals are a red light and a green light respectively;

the wearing state is divided into three levels, and a higher level corresponds to better wearing quality;

the difference value is equal to a signal amount of reflected light corresponding to the green light minus a signal amount of reflected light corresponding to the red light;

the two preset first signal amount thresholds are a first threshold and a second threshold respectively, wherein the first threshold is greater than the second threshold;

when the difference value is greater than or equal to the first threshold, further determining the change trend of the difference value; determining the wearing state as a third-level wearing state when the difference value continuously increases; returning to determine the relationship between the difference value and the first threshold when the difference value continuously decreases or is unchanged;

when the difference value is greater than the second threshold and less than the first threshold, further determining the change trend of the difference value; determining the wearing state as a second-level wearing state when the difference value is unchanged or decreases; returning to determine the relationship between the difference value and the second threshold when the difference value continuously increases; and when the difference value is less than or equal to the second threshold, determining the wearing state as a first-level wearing state.

* * * * *